United States Patent
Fix et al.

(10) Patent No.: US 9,651,512 B2
(45) Date of Patent: May 16, 2017

(54) GAS SENSOR

(71) Applicant: Robert Bosch GmbH, Stuttgart (DE)

(72) Inventors: Richard Fix, Gerlingen (DE); Denis Kunz, Untergruppenbach (DE); Philipp Nolte, Gerlingen (DE); Katrin Luckert, Leonberg (DE)

(73) Assignee: ROBERT BOSCH GMBH, Stuttgart (DE)

( * ) Notice: Subject to any disclaimer, the term of this patent is extended or adjusted under 35 U.S.C. 154(b) by 330 days.

(21) Appl. No.: 14/314,803

(22) Filed: Jun. 25, 2014

(65) Prior Publication Data

US 2015/0001095 A1    Jan. 1, 2015

(30) Foreign Application Priority Data

Jun. 27, 2013   (DE) .................... 10 2013 212 478

(51) Int. Cl.
| | |
|---|---|
| *G01N 27/00* | (2006.01) |
| *G01N 7/00* | (2006.01) |
| *G01N 21/00* | (2006.01) |
| *G01N 31/00* | (2006.01) |
| *G01N 33/00* | (2006.01) |
| *G01N 35/00* | (2006.01) |
| *G01N 27/12* | (2006.01) |

(52) U.S. Cl.
CPC .................... *G01N 27/12* (2013.01)

(58) Field of Classification Search
CPC .......... G01N 27/00; G01N 7/00; G01N 21/00; G01N 31/00; G01N 33/00; G01N 35/00
USPC ..... 422/83, 98, 82.02, 94; 436/43, 181, 106, 436/127, 139, 144, 145; 73/23.2, 1.02, 73/31.05, 31.06
See application file for complete search history.

(56) References Cited

U.S. PATENT DOCUMENTS

| | | | | |
|---|---|---|---|---|
| 3,649,156 | A | * | 3/1972 | Conner ........................ 431/78 |
| 3,801,972 | A | * | 4/1974 | Ho Kim et al. ............. 340/510 |
| 4,263,886 | A | * | 4/1981 | Batchelor ................. 126/116 A |
| 4,326,199 | A | * | 4/1982 | Tarpley et al. ............. 340/622 |

(Continued)

FOREIGN PATENT DOCUMENTS

DE         36 07 065        9/1986

*Primary Examiner* — Brian J Sines
(74) *Attorney, Agent, or Firm* — Gerard Messina

(57) ABSTRACT

A device, a method, and a use thereof for detecting a concentration of a gas or of a gas component. The device as a gas sensor includes at least one sensor element including a gas-sensitive layer and a heating element for heating the gas-sensitive layer. The heating element is able to heat the sensitive layer to a desired temperature prior to the detection and/or is able to maintain it at a desired temperature during the detection. The heating element allows the gas-sensitive layer to be outgassed if needed, so as to allow absorption again. To heat the heating element, there is a first contacting to which a first voltage may be applied. Moreover, subsequent to the heating step, a second voltage may be applied to the sensor element or to the gas-sensitive layer for measured value detection with the aid of a second contacting. The two contactings at least partially have a shared actuation by being electrically connected to each other, the first contacting including a diode which essentially blocks current from flowing through the heating element when the second voltage, in particular the polarity of the second voltage, is applied.

18 Claims, 3 Drawing Sheets

(56) References Cited

U.S. PATENT DOCUMENTS

| | | | |
|---|---|---|---|
| 4,348,583 A * | 9/1982 | Bube et al. | 219/497 |
| 4,410,632 A * | 10/1983 | Dilley et al. | 436/20 |
| 4,414,839 A * | 11/1983 | Dilley et al. | 73/23.4 |
| 4,564,748 A * | 1/1986 | Gupton | 219/497 |
| 4,644,138 A * | 2/1987 | Walsh | 219/501 |
| 2008/0023464 A1 * | 1/2008 | Otto et al. | 219/481 |

\* cited by examiner

GAS SENSOR

RELATED APPLICATION INFORMATION

The present application claims priority to and the benefit of German patent application no. 10 2013 212 478.3, which was filed in Germany on Jun. 27, 2013, the disclosure of which is incorporated herein by reference.

FIELD OF THE INVENTION

The present invention relates to a device and a method for detecting a concentration of a gas or of a gas component, and to the use of such a device or of such a method.

BACKGROUND INFORMATION

Gas sensors made of semiconducting metal oxides or of organic or polymer layers as sensitive material for the detection of gases, or certain components of a gas, are known. The signal evaluation is carried out in the corresponding sensor element by measuring the induced changes of the conductivity, the capacity and/or the escape function based on the presence of the gas or select gas components. To improve the sensor function and/or regeneration, gas sensors are usually operated with an additional heating element at elevated temperatures, generally in the temperature range between 150° C. and 500° C. These heating elements may be applied to the substrate but may also be integrated directly into the substrate. Two connections are provided in each case for controlling the sensitive gas sensor element and the heating element, so that the two elements may be controlled independently of each other.

A gas sensor is known from the publication DE 36 07 065 A1, in which a sensing element made of a metal oxide semiconductor material and a heating element is provided. To detect the instantaneous state of the surroundings, the electrical resistance value of the sensing element during a time period is established, during which the sensing element is not heated by the heating element.

SUMMARY OF THE INVENTION

A device and a method for detecting a concentration of a gas or of a gas component and the use of such a device or of such a method are described hereafter. It is provided for this purpose that the device configured as a gas sensor includes at least one sensor element including a gas-sensitive layer and a heating element for heating the gas-sensitive layer. The heating element is configured for this purpose in such a way that it is able to heat the sensitive layer to a desired temperature prior to the detection and/or is able to maintain it at a desired temperature during the detection. Moreover, the heating element also allows the gas-sensitive layer to be outgassed if needed, e.g., to allow absorption again. To heat the heating element, a first contacting is provided, to which a first voltage may be applied. Moreover, subsequent to the heating step, a second voltage may be applied to the sensor element or to the gas-sensitive layer for the measured value detection with the aid of a second contacting. The core of the present invention is now that the two contactings at least partially have a shared actuation by being electrically connected to each other, the first contacting including a diode which essentially blocks current from flowing through the heating element when the second voltage, in particular the polarity of the second voltage, is applied.

The two elements (heating element and sensor element) may thus be directly connected to a shared voltage source; however, they may be operated separately from each other at least partially via the different level and/or polarity of the actuation. As a result of the shared actuation, the complete separate implementation of a second actuation circuit is thus additionally avoidable, so that a more compact gas sensor is made possible.

Optionally, an evaluation unit may also be provided, which derives a concentration of a gas or of a gas component from the measured value detection as a function of the actuation of the sensor element. If necessary, the detection of the temperature during the heating of the heating element when the first voltage is applied and/or during the measured value detection when the second voltage is applied may also be used for this purpose.

In one particular embodiment of the present invention, the gas sensor is manufactured at least partially using a micromechanical design. For this purpose, the sensitive layer of the sensor element may be applied to the surface of a semiconductor substrate, e.g., adjoining a diaphragm. The heating element may be directly integrated into the semiconductor substrate for this purpose, or it may also be accommodated on a surface of the semiconductor substrate in the vicinity of the sensitive layer, e.g., on the opposite side of the semiconductor substrate. The contacting of the heating element and of the sensor element, or of the gas-sensitive layer, may take place with the aid of external bond joints in which one diode is connected upstream from the heating element. However, as an alternative it may also be provided that a connection between the contacting or actuation of the heating element and of the sensor element takes place directly by the semiconductor substrate. The semiconductor substrate may thus be made of differently doped and, if necessary, buried layers over a large surface area, or also over a limited area, e.g., in a via, so that a p-n junction is formed. This p-n junction in the substrate may then also be used as a diode for connecting the heating element.

To operate the gas sensor, it is provided that, in a first step, the first voltage, with which the heating element is operated, exceeds the breakdown voltage or threshold voltage of the diode. In this way, a current flow through the heating element is enabled, despite the application of a voltage which is present on the diode in the reverse direction. While in this case a current also flows through the gas-sensitive layer, this current and the magnitudes are lower than those through the heating element. In a directly subsequent second step, if necessary, the voltage is reduced in such a way that it drops below the reverse voltage of the diode to derive a detection of a suitable measured variable for derivation of a concentration of the surrounding gas or of the gas component. Due to the blocking action of the diode, the essential portion of the current flows through the sensor element, and thus through the gas-sensitive layer.

In the above-mentioned embodiment of the present invention, it is provided that the actuation of the heating element and of the sensor element is carried out with the aid of a DC voltage. However, it is also possible to heat the heating element with the aid of an AC voltage and to use a DC voltage for detecting the concentration variable.

It may also be provided as one refinement of the present invention that multiple diodes are connected in series. However, care must be taken here that the first voltage used in the first step must be selected to be greater than the sum of the breakdown voltages or threshold voltages to enable a current flow.

Of course, it may be provided that the sensor according to the present invention is able to detect further variables, in addition to detecting the concentration of a gas or of a gas component. It may be provided that multiple gas components are detectable consecutively by different actuation and, if necessary, outgassing processes of the gas-sensitive layer. In addition, however, it is also possible to detect further measured variables using other sensor elements and to combine these with the detected gas sensor measured variable.

The provided present invention is usable in consumer products, such as mobile terminals, among other things. For example, it is conceivable to accommodate the device in a mobile phone or a smart phone to be able to carry out mobile air or breathing gas analyses. Similar applications are also possible for devices in medical technology (such as lab-on-chip analytics), in household appliances, and for use in motor vehicles (such as exhaust gas analysis).

Further advantages are derived from the following description of exemplary embodiments and from the dependent patent claims.

DETAILED DESCRIPTION

As described at the outset, an accordingly sensitive sensor element is required for the detection of a gas or gas components. Such gas-sensitive sensor elements may include materials whose electrical resistance changes as a function of the surrounding gas atmosphere (semiconducting metal oxides, organic or polymer compounds). To increase the sensitivity of the sensor element or to restore the regeneration following the absorption of gases or gas components, however, it is also possible to deliberately heat only the sensitive sensor element of the entire sensor device with the aid of one heating element, such as a meander-shaped metal conductor.

Figure 1:
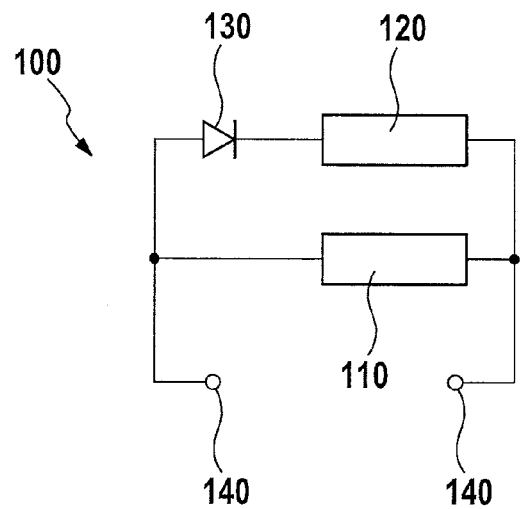
FIG. 1 is a schematic illustration of a block diagram of the device according to the present invention.

According to FIG. 1a, the principle of the present invention is described based on a device 100 in which the gas-sensitive sensor element 110 required for a gas sensor is heatable by an assigned heating element 120. It is provided in particular that two elements 110 and 120 may be operated by the same (DC) voltage source 140, if necessary via the same contacts. However, to be able to carry out the detection or establishment of the concentration of the desired gas component, a separate operation of gas-sensitive sensor element 110, independently of a heating by heating element 120, is required. For this purpose, according to the present invention a diode 130 is added to the connection of heating element 120, and the entire device is operated using at least two different voltages $U_1$ and $U_2$ of a DC voltage source 140, the polarity of DC voltage source 140 being provided in such a way that it is applied in the forward direction of diode 130, at least one voltage being selected below the threshold voltage of the diode, and at least one further voltage being selected above the threshold voltage.

Optionally, it is also possible to apply the DC voltage in such a way that the first voltage is applied in the forward direction and the second voltage is applied in the reverse direction of the diode. An additional control element of the voltage source is provided for this purpose.

Figure 2:
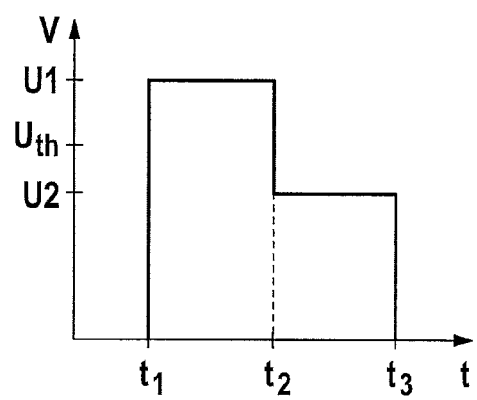
FIG. 2, in contrast, shows a flow chart of the underlying method.

Device 100 according to FIG. 1b is operated in two phases (see FIG. 2). In a first (operating) phase between $t_1$ and $t_2$, a (DC) voltage U1 is used, which is above the breakdown voltage or threshold voltage of diode 130. The circuit is thus connected through via heating element 120 so that it may heat up. As a result of the provided thermal contact between heating element 120 and gas-sensitive sensor element 110, sensor element 110 is also heated thereby, e.g., to the desired operating temperature.

While the resistance of a typical heating element is in the range of $0.1\Omega$ to $1000\Omega$, which may be in the range of $1\Omega$ to $100\Omega$, the resistance of gas-sensitive sensor element 110 is typically greater by several orders of magnitude. In this way, resistance values in the range of $10\,k\Omega$ to $1000\,k\Omega$ may be present for the material of the gas-sensitive sensor element. Since a considerably higher resistance is thus present for sensor element 110 than for heating element 120, no significant current flows through gas-sensitive sensor element 110 in this first phase. The heating of sensor element 110 thus essentially takes place by the thermal contact with heating element 120.

In the second (operating) phase between t2 and t3, the applied (DC) voltage U2 is reduced in such a way that it is below the threshold voltage Uth. This causes diode 130 to block, so that the entire current flows through gas-sensitive sensor element 110. This second phase is thus usable for measuring the gas concentration. A characteristic resistance of the gas-sensitive element, and thus a characteristic current, develops as a function of the surrounding gas atmosphere.

No heating of the gas-sensitive element takes place during the second phase of the measured value detection. However, typically a dependency exists between the gas sensitivity of the gas-sensitive layer which is used and its temperature. The achieved or set temperature of sensor element 110 in the first phase therefore must be considered in the measured value detection. Depending on the specific embodiment of the heating/sensor system, this dependency must be considered accordingly in the measurement of the gas concentration.

Figure 3A:
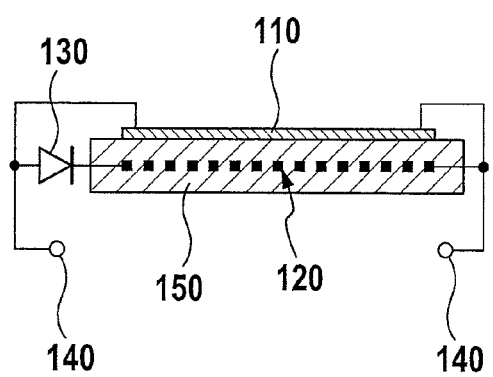
FIG. 3A, a specific embodiment of the arrangement of the heating and sensor elements when implementing a gas sensor in a semiconductor substrate.
Figure 3B:
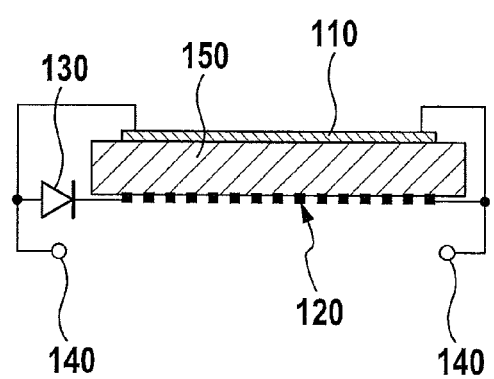
FIG. 3B, a specific embodiment of the arrangement of the heating and sensor elements when implementing a gas sensor in a semiconductor substrate.

FIGS. 3a and 3b show two possible specific embodiments of the arrangements of the heating and sensor elements when implementing a gas sensor in a semiconductor substrate. As is apparent from FIG. 3a, a gas-sensitive sensor layer 110 is applied to a semiconductor substrate 150, the layer allowing corresponding concentrations of predetermined gas components to be detected with the aid of an evaluation circuit which is not shown. Heating element 120 is a separate element in this exemplary embodiment and is directly embedded into substrate 150. FIG. 3b shows an alternative in which heating element 120 is applied to the side of substrate 150 situated opposite gas-sensitive sensor layer 120 [sic; 110]. Due to diode 130 connected to DC voltage source 140 in the forward direction, separate heating and measured value detection are possible using the above-described actuation method. The high thermal capacity of the substrate additionally makes it possible that temperature changes take place so sluggishly after deactivation of the heating element that no significant temperature change of gas-sensitive layer 110 takes place within the necessary time [for the] measured value detection. In this way, also no significant influences result on the sensitivity of the used gas-sensitive layer.

Figure 4A:
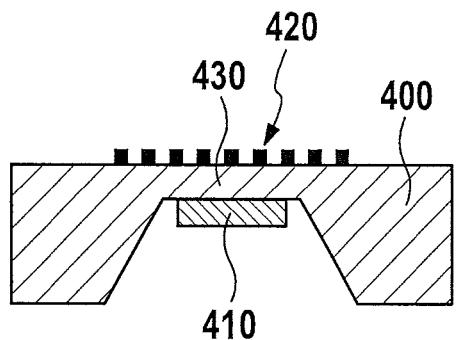
FIGS. 4A, 4B, 4C, 4D, shows specific embodiments of the arrangements of the heating element and sensor element when using a thin-film diaphragm.
Figure 4B:
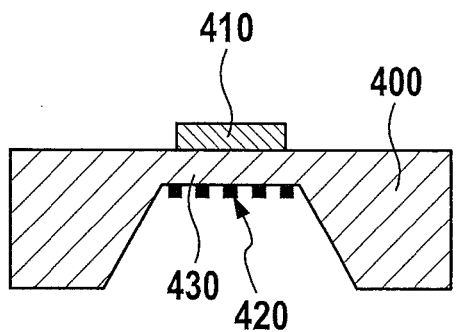
Figure 4C:
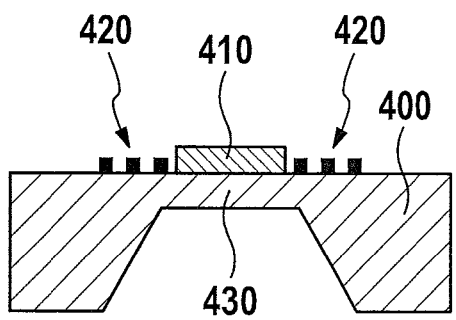
Figure 4D:
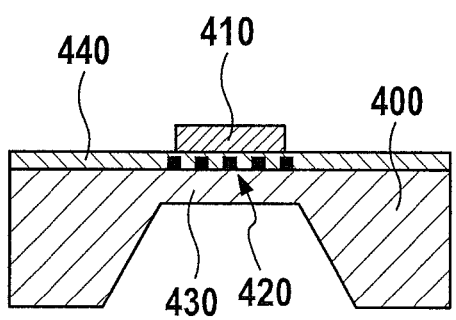

FIGS. 4a through 4d show further specific embodiments of the arrangement of the heating element and sensor element when using a thin-film diaphragm. For example, FIG. 4a shows a thin-film diaphragm 430 in a semiconductor substrate 400 in which gas-sensitive layer 410 is situated in a recess of substrate 400 beneath thin-film diaphragm 430. In contrast, heating element 420 is provided on the opposite side of thin-film diaphragm 430. The electrical contacting or the actuation of the two elements takes place as described above via the upstream connection of a diode during the actuation of the heating element in the reverse direction. FIGS. 4b through 4c show different variants of the arrangement of heating element 420 and sensitive layer 410 in the area of thin-film diaphragm 430, additionally also an electrically insulated layer 440 being providable, into which heating element 430 may be embedded.

Due to the low thermal mass of thin-film diaphragm 430, gas-sensitive layer 410 heated by heating element 420 cools off immediately after the heating element is deactivated. To enable a clear evaluation of the measured value recording, knowledge of the temperature progression of gas-sensitive layer 410 during the measured value recording in the second phase and, if necessary, also during the heating in the first phase is required. This is due to the nature of the adsorption of gas species on the gas-sensitive layer and, if necessary, of subsequently occurring signal-generating electrochemical processes (e.g., dissociation, chemisorption) being highly temperature-dependent. To allow a clear and reproducible measured value detection, it is necessary to consider the temperature progressions from the two phases.

To be able to set the sensor system exactly to a desired target temperature or to be able to carry out a particular temperature profile, the heating element must be regulated based on a temperature measurement. This temperature measurement may be carried out, for example, via a resistance measurement of the parallel connection of the sensor element and heating element and diode. Since the resistance of the parallel connection changes characteristically as a function of the temperature, the temperature is determinable from the measured resistance following a one-time calibration.

Figure 5:
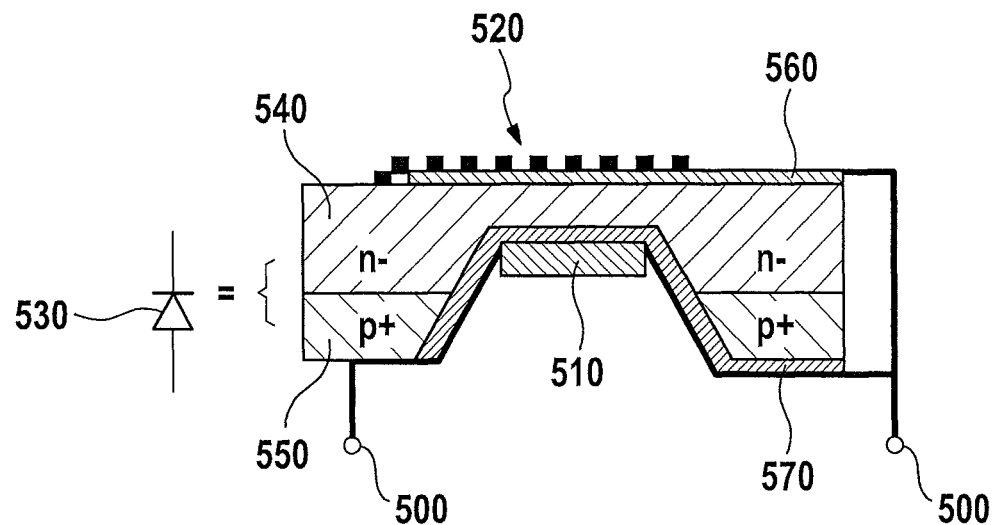
FIG. 5, a semiconductor substrate having a thin-film diaphragm.

In one further specific embodiment, diode 530 may be formed directly in the semiconductor substrate. As is shown in FIG. 5, a semiconductor substrate having a thin-film diaphragm may be used for this purpose, corresponding to the specific embodiments of FIGS. 4a through 4d. In the present exemplary embodiment, gas-sensitive layer 510 is applied to an electrically insulating layer 570 beneath the thin-film diaphragm, and heating element 520 is applied also to an electrically insulating layer 560 above the thin-film diaphragm. To implement diode 530 directly in the substrate, the substrate is divided into layers 540 and 550, which in each case have opposite doping, so that a p-n junction is present. An intrinsic diode 530 is thus generated in the substrate, which allows the above-described two-phase actuation using appropriate circuitry.

Specifically, in the exemplary embodiment according to FIG. 5, the substrate is divided into an upper, doped n– layer 540, which is assigned to heating element 520, and a lower, doped p+ layer 550, which is assigned to gas-sensitive layer 510. Using aforementioned electrically insulated layers 560 and 570, the contact may be applied in each case to doped n– layer 540 via heating element 520 and to doped p+ layer 550 via gas-sensitive layer 510. If a DC voltage 500 is now applied to the substrate, so that present layers 540 and 550 are operated in the reverse direction, the method according to the present invention is usable for actuating the heating/sensor system according to the description above.

As is apparent from FIG. 5, the p-n junction may be implemented outside the heated area to avoid disturbances of the diode behavior due to temperature changes or due to excessively high temperatures. In fact, it is advantageous to configure the entire thin-film diaphragm using a uniform doping or doping type.

Figure 6:
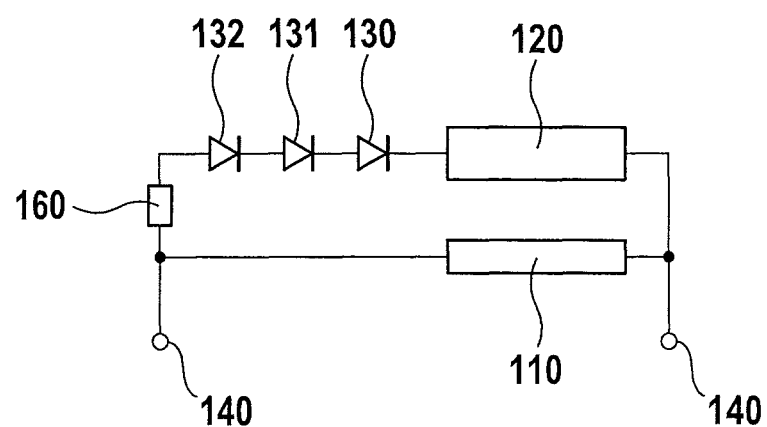
FIG. 6, a specific embodiment, using one or multiple diodes in series.

One further specific embodiment (see FIG. 6) is to additionally use one or multiple diodes in series (diode cascade). In this way, the activation voltage of the heating element may be shifted toward higher voltages ($U_{th1}+U_{th2}+\ldots$). This may be favorable when a voltage which already exceeds the threshold voltage of a single diode is required for the measured value detection of the gas-sensitive element. Optionally, a current limiting element 160 may be provided both in the above-described embodiment according to FIG. 6, and in the other embodiments, to prevent the diodes from being destroyed.

In general, the forward resistance of the diode should be considerably smaller than the heating resistance, since otherwise too much output would be converted into heat within the diode.

To adapt the sensor system to the above-mentioned conditions, it may be favorable to use Zener diodes in the reverse direction. They are characterized by a low resistance when voltages above the breakdown voltage or threshold voltage are applied.

In the description above, a resistive sensor element has been mentioned by way of example as the gas-sensitive layer, i.e., a sensor element in which the resistance changes as a function of the gas surroundings. It is also possible, of course, to apply the described system and the described method analogously to further measuring principles for gas detection. For example, the sensor element may be made from an ion conductor, on which a Nernst voltage is measurable when different gas concentrations exist between gas chamber 1 and gas chamber 2 (in this regard, see DE 10 2012 201304 A1). In the second phase of the measured value detection, in this case the Nernst voltage or the pump current is measured (instead of measuring the current). A gas-sensitive field-effect transistor is also usable as the sensor element. Here, the channel current and/or the gate voltage would be detected accordingly as the sensor signal in the second phase.

According to the present specific embodiments, the two contactings or circuit systems for operating the heating element and the sensor element are supplied with voltage with the aid of a voltage source 140. For connecting these contactings, it is provided in one particular embodiment that only two contacts are provided, via which the two electrical contactings or circuits are supplied. It may be provided for this purpose that these contacts are provided directly on the semiconductor substrate, so that they are easily electrically contactable with the aid of a bond joint.

In one further embodiment of the present invention, it is provided that the voltage source is able to generate both a DC voltage and an AC voltage. It may thus be provided that the heating element is heated with the aid of an AC voltage in the first phase, it being provided that, in particular, the magnitude of the AC voltage exceeds the breakdown voltage or the threshold voltage. In contrast, a DC voltage is still provided for the measured value detection in the second phase.

As an alternative, it may be also be provided that a basic DC voltage is provided at a level at which the diode blocks. An AC voltage may then be modulated upward in the first phase, with the aid of which the breakdown voltage or threshold voltage of the diode is achieved.

It is provided in one specific embodiment of the present invention that the sensor element including the gas-sensitive layer, the heating element and the evaluation arrangement, which derives the concentration of the gas and/or of the gas component from the concentration variable, are accommodated on a shared carrier element or in a shared housing. Optionally, it is also possible to provide one or multiple temperature sensors, which detects/detect the temperature of the gas-sensitive layer and/or of the heating element and may be used for the derivation of the concentration.

A possible use of the described present invention takes place in a mobile terminal, e.g., in a mobile phone or a smart phone. For example, it is conceivable that the mobile terminal includes an air inlet, which may be directed in the direction of the gas to be measured, e.g., as part of a lab-on-chip method. Alternatively, the air inlet may also be configured in such a way that it is possible to blow into it to be able to carry out a breathing gas analysis.

What is claimed is:

1. A device for detecting a concentration of a gas or of a gas component, comprising:
    a sensor element including a gas-sensitive layer; and
    a heating element for heating the gas-sensitive layer;
    wherein a first voltage is applied to the heating element for heating the gas-sensitive layer with the aid of a first electrical contacting,
    wherein a second voltage is applied to the sensor element for detecting a concentration variable representing the concentration of the gas or of the gas component with the aid of a second contacting, and
    wherein the first and second contactings are electrically connected to each other, and the first electrical contacting includes a diode, which essentially blocks the flow of current through the heating element when the second voltage is applied.

2. The device of claim 1, wherein the gas-sensitive layer is situated on the surface of a semiconductor substrate, the connection of the second contacting to the first contacting being carried out at least partially by the semiconductor substrate.

3. The device of claim 2, wherein the p-n junction is created by buried p-doped and n-doped layers.

4. The device of claim 1, wherein the first voltage is greater than the breakdown voltage or threshold voltage of the diode.

5. The device of claim 1, wherein at least two diodes connected in series are provided in the first contacting.

6. The device of claim 1, wherein the first and second contactings include at least two shared contacts, the first and second voltages being applied with the aid of the in particular one voltage source.

7. The device of claim 1, wherein the first and second voltages have different polarities.

8. The device of claim 1, wherein there is at least one detecting arrangement for detecting a temperature variable representing the temperature of the heating element and/or of the sensitive layer, and wherein the detection of the concentration of the gas or of the gas component is carried out as a function of the detected temperature variable.

9. A method for detecting a concentration of a gas or of a gas component, the method comprising:
    providing a device for detecting the concentration of the gas or of the gas component, the device including a sensor element including a gas-sensitive layer, and a heating element for heating the gas-sensitive layer, the device being operable to perform the following:
    applying a first voltage via a first electrical contacting to the heating element for heating the gas-sensitive layer;
    applying a second voltage via a second electrical contacting to the sensor element for detecting the concentration of the gas or of the gas component; and
    detecting a concentration variable representing the concentration of the gas or of the gas component;
    wherein the first and second contactings are electrically connected to each other, and the second voltage is selected so that it essentially blocks current from flowing through the heating element by a diode provided in the first electrical contacting.

10. The method of claim 9, wherein the first voltage is selected to be greater than the breakdown voltage or threshold voltage of the diode, and wherein the second voltage is smaller than the breakdown voltage or threshold voltage of the diode.

11. The method of claim 9, wherein a temperature variable is detected which represents the temperature of the heating element and/or of the sensitive layer when the first voltage and/or second voltage is/are applied, the derivation of the concentration of the gas or the gas component being carried out as a function of the concentration variable and the temperature variable.

12. The method of claim 9, wherein different polarities are used for the first and second (DC) voltages.

13. A mobile processor device, comprising:
    a device for detecting a concentration of a gas or of a gas component, including:
    a sensor element including a gas-sensitive layer; and
    a heating element for heating the gas-sensitive layer;
    wherein a first voltage is applied to the heating element for heating the gas-sensitive layer with the aid of a first electrical contacting,
    wherein a second voltage is applied to the sensor element for detecting a concentration variable representing the concentration of the gas or of the gas component with the aid of a second contacting, and
    wherein the first and second contactings are electrically connected to each other, and the first electrical contacting includes a diode, which essentially blocks the flow of current through the heating element when the second voltage is applied.

14. The mobile processor device of claim 13, wherein the mobile processor device includes a mobile terminal, a mobile phone, a smart phone, a tablet PC or a portable computer.

15. The device of claim 1, wherein the gas-sensitive layer is situated on the surface of a semiconductor substrate, the connection of the second contacting to the first contacting being carried out at least partially by the semiconductor substrate, and it being provided that the connection is created in the form of a p-n junction of the doped semiconductor material.

16. The device of claim 1, wherein the first voltage is greater than the breakdown voltage or threshold voltage of the diode, the second voltage being smaller than the breakdown voltage or threshold voltage of the diode.

17. The device of claim 1, wherein at least two diodes connected in series are provided in the first contacting, the first voltage being greater than the sum of the breakdown voltage or threshold voltage of the diodes which are connected in series.

18. The device of claim 1, wherein the first and second voltages have different polarities, and wherein there is one switching arrangement which switches the polarity of the voltage source.

* * * * *